United States Patent [19]

Ramirez

[11] Patent Number: 5,692,524

[45] Date of Patent: Dec. 2, 1997

[54] ADJUSTABLE POST MORTEM CHIN STRAP

[76] Inventor: Adrianna Ramirez, 16922 PCH #103, Huntington Beach, Calif. 92649

[21] Appl. No.: 723,343

[22] Filed: Sep. 30, 1996

[51] Int. Cl.$^6$ .................................................. A61F 5/37
[52] U.S. Cl. .......................... 128/876; 128/848; 602/18; 606/204.35
[58] Field of Search ........................ 128/857, 858, 128/848; 602/17, 18, 74; 606/204.15, 204.35

[56] References Cited

U.S. PATENT DOCUMENTS

| | | | |
|---|---|---|---|
| 724,812 | 4/1903 | Cloud | 606/204.35 |
| 815,426 | 3/1906 | Hardee | 606/204.35 |
| 3,312,217 | 4/1967 | McKinstry | 128/857 |
| 4,694,823 | 9/1987 | Young | 606/204.35 |
| 5,284,469 | 2/1994 | Jasen | 602/17 |

*Primary Examiner*—Michael A. Brown

[57] ABSTRACT

A new Adjustable Post Mortem Chin Strap for facilitating retention of a deceased's lower jaw in the closed position during presentations. The inventive device includes a chin strap that engages the lower jaw, a right loop an end of the chin strap and engaging the right ear, and a left loop secured to the end of the chin strap opposite of the right loop and engaging the left ear thereby resiliently biasing the chin strap against the lower jaw. The invention is adjustable to various sizes of heads and may be quickly adjusted to maintain the preferred appearance of the deceased.

6 Claims, 3 Drawing Sheets

5,692,524

ADJUSTABLE POST MORTEM CHIN STRAP

BACKGROUND OF THE INVENTION

1. Field of the Invention

The present invention relates to Head Support Devices and more particularly pertains to a new Adjustable Post Mortem Chin Strap for facilitating retention of a deceased's lower jaw in the closed position during presentations.

2. Description of the Prior Art

The use of Head Support Devices is known in the prior art. More specifically, Head Support Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Head Support Devices include U.S. Pat. No. 5,388,592; U.S. Pat. No. 4,084,585; U.S. Design Pat. No. 354,346; U.S. Pat. No. 5,320,112; U.S. Pat. No. 4,195,629 and U.S. Pat. No. 4,941,470.

While these devices fulfill their respective, particular objectives and requirements, the aforementioned patents do not disclose a new Adjustable Post Mortem Chin Strap. The inventive device includes a chin strap that engages the lower jaw, a right loop an end of the chin strap and engaging the right ear, and a left loop secured to the end of the chin strap opposite of the right loop and engaging the left ear thereby resiliently biasing the chin strap against the lower jaw.

In these respects, the Adjustable Post Mortem Chin Strap according to the present invention substantially departs from the conventional concepts and designs of the prior art, and in so doing provides an apparatus primarily developed for the purpose of facilitating retention of a deceased's lower jaw in the closed position during presentations.

SUMMARY OF THE INVENTION

In view of the foregoing disadvantages inherent in the known types of Head Support Devices now present in the prior art, the present invention provides a new Adjustable Post Mortem Chin Strap construction wherein the same can be utilized for facilitating retention of a deceased's lower jaw in the closed position during presentations.

The general purpose of the present invention, which will be described subsequently in greater detail, is to provide a new Adjustable Post Mortem Chin Strap apparatus and method which has many of the advantages of the Head Support Devices mentioned heretofore and many novel features that result in a new Adjustable Post Mortem Chin Strap which is not anticipated, rendered obvious, suggested, or even implied by any of the prior art Head Support Devices, either alone or in any combination thereof.

To attain this, the present invention generally comprises a chin strap that engages the lower jaw, a right loop an end of the chin strap and engaging the right ear, and a left loop secured to the end of the chin strap opposite of the right loop and engaging the left ear thereby resiliently biasing the chin strap against the lower jaw.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, tire purpose of the foregoing abstract is to enable tire U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Adjustable Post Mortem Chin Strap apparatus and method which has many of the advantages of the Head Support Devices mentioned heretofore and many novel features that result in a new Adjustable Post Mortem Chin Strap which is not anticipated, rendered obvious, suggested, or even implied by any of the prior art Head Support Devices, either alone or in any combination thereof.

It is another object of the present invention to provide a new Adjustable Post Mortem Chin Strap which may be easily and efficiently manufactured and marketed.

It is a further object of the present invention to provide a new Adjustable Post Mortem Chin Strap which is of a durable and reliable construction.

An even further object of the present invention is to provide a new Adjustable Post Mortem Chin Strap which is susceptible of a low cost of manufacture with regard to both materials and labor, and which accordingly is then susceptible of low prices of sale to the consuming public, thereby making such Adjustable Post Mortem Chin Strap economically available to the buying public.

Still yet another object of the present invention is to provide a new Adjustable Post Mortem Chin Strap which provides in the apparatuses and methods of the prior art some of the advantages thereof, while simultaneously overcoming some of the disadvantages normally associated therewith.

Still another object of the present invention is to provide a new Adjustable Post Mortem Chin Strap for facilitating retention of a deceased's lower jaw in the closed position during presentations.

Yet another object of the present invention is to provide a new Adjustable Post Mortem Chin Strap which includes a chin strap that engages the lower jaw, a right loop an end of the chin strap and engaging the right ear, and a left loop secured to the end of the chin strap opposite of the right loop and engaging the left ear thereby resiliently biasing the chin strap against the lower jaw.

Still yet another object of the present invention is to provide a new Adjustable Post Mortem Chin Strap that allows for the quick adjustment to various sizes of deceased's heads.

Even still another object of the present invention is to provide a new Adjustable Post Mortem Chin Strap that retains the mouth closed at all times for appearance during memorial services.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 2:
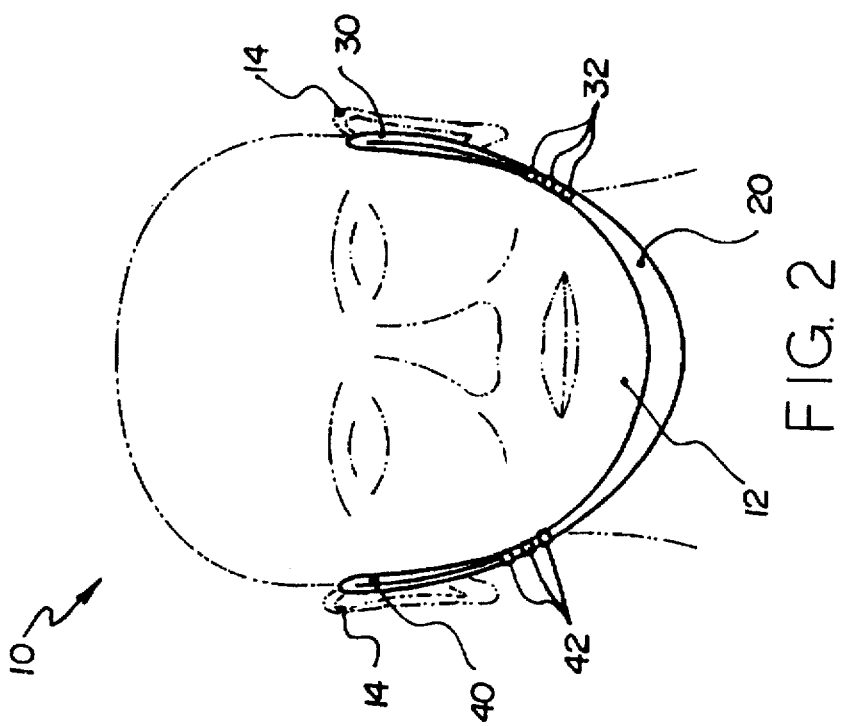
FIG. 2 is a front view thereof.

With reference now to the drawings, and in particular to FIG. 1 through 6 thereof, a new Adjustable Post Mortem Chin Strap embodying the principles and concepts of the present invention and generally designated by the reference numeral 10 will be described.

More specifically, it will be noted that the Adjustable Post Mortem Chin Strap 10 comprises a chin strap 20 juxtaposed to a lower jaw 12, a right ear loop 30 secured and closed to an end of the chin strap 20, where the right ear loop 30 removably engages the deceased's right ear 14, and a left ear loop 40 secured and closed to the end of the chin strap 20 opposite of the right ear loop 30, where the left ear loop 40 removably engages the deceased's left ear 14 thereby resiliently biasing the chin strap 20 against the lower jaw 12 in a closed position.

Figure 1:
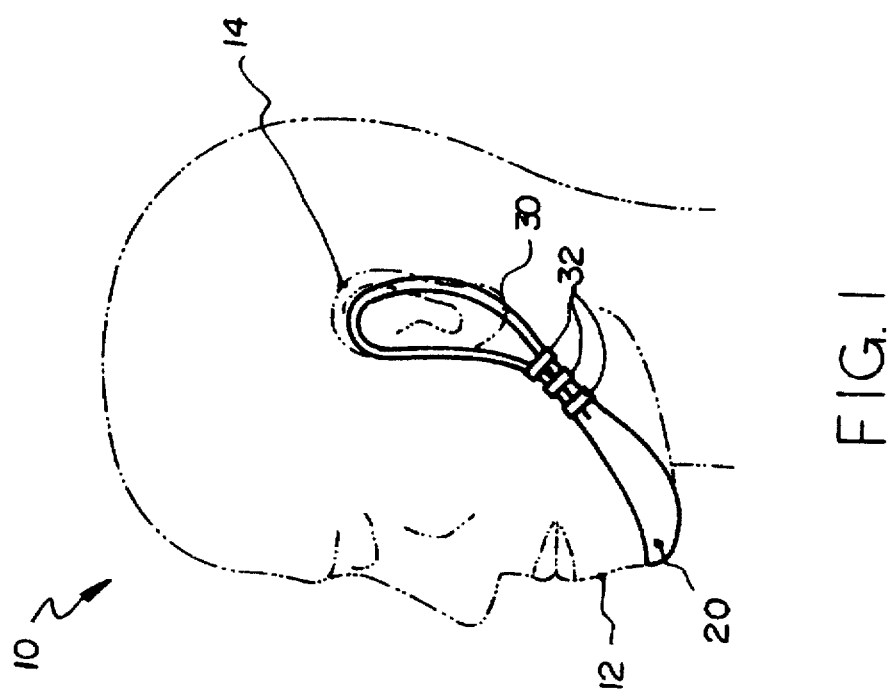
FIG. 1 is a right side view of a new Adjustable Post Mortem Chin Strap according to the present invention.
Figure 3:
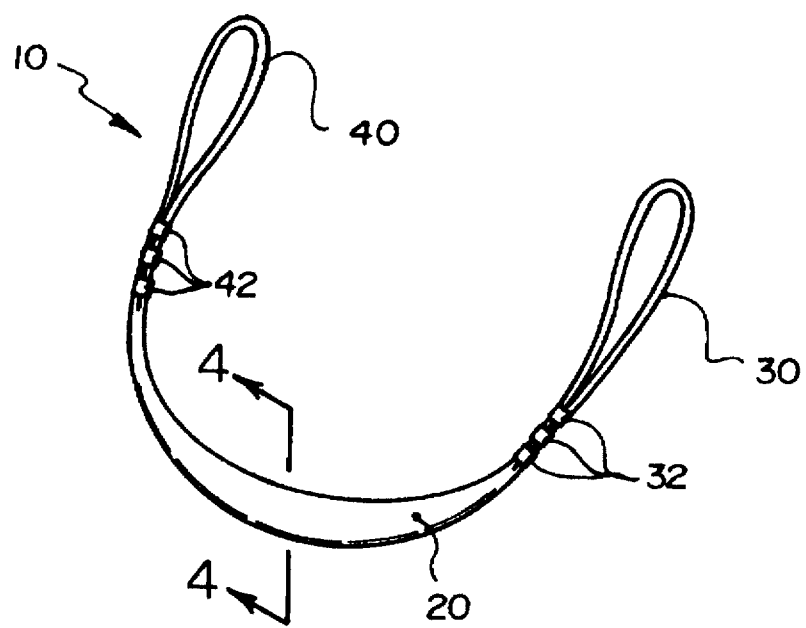
FIG. 3 is a perspective view of the present invention.
Figure 4:
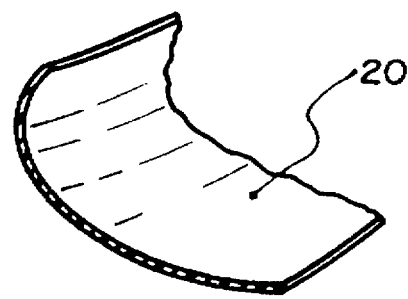
FIG. 4 is a cross sectional view taken along line 4—4 of FIG. 3.
Figure 5:
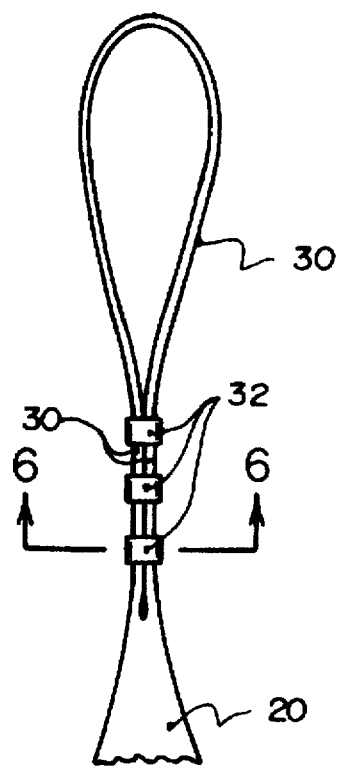
FIG. 5 is a magnified right side view of the right ear loop and right bands.
Figure 6:
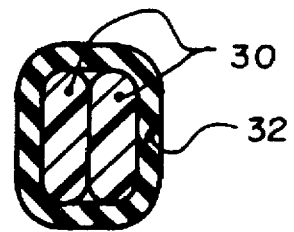
FIG. 6 is a cross sectional view taken along line 6—6 of FIG. 5.

As best illustrated in FIGS. 1 through 3, it can be shown at least one right band 32 slidably surrounds the right ear loop 30 mesial the right ear 14 and the chin strap 20. The right band 32 allows the user to adjust length and tension of the present invention against the lower jaw 12 to fit various sizes of heads. As shown in FIGS. 2 and 3, at least one left band 42 slidably surrounds the left ear loop 40 mesial the left ear 14 and the chin strap 20. The left hand 42 allows the user to adjust length and tension of the present invention against the lower jaw 12 to fit various sizes of heads. As best shown in FIG. 4 of the drawings, the central portion of the chin strap 20 is formed into an arcuate shape formed to the shape of the lower jaw 12 for increased stability and gripping of the lower jaw 12 to prevent slippage. The extended ends of the chin strap 20 preferably taper into narrow swaged sections as shown in FIGS 1 through 3 and 5 of the drawings. The chin strap 20 preferably is constructed from a transparent resilient plastic. The chin strap 20 in an alternative embodiment would be constructed from a tinted resilient plastic. The right ear loop 30 and the left ear loop 40 preferably are constructed from an elastic material providing constant resilient bias against the lower jaw 12 by the present invention. As shown in FIGS. 1 through 3, there are preferably three right bands 32 spaced apart. As shown in FIGS. 2 and 3 of the drawings, there are preferably three left bands 42 spaced apart providing increased adjustment of the present invention and increased aesthetics.

In use, the user positions the interior curvature portion of the chin strap 20 juxtaposed to the deceased's lower jaw 12. The right and left ear loops 30, 40 engage the respective ears 14. The right and left bands 32, 42 are slidably positioned about the right and left ear loops 30, 40 to achieve the desired tension against the lower jaw 12 of the deceased to retain the mouth closed. The lower chin 12 is thereby maintained in the closed position until the present invention is removed.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An Adjustable Post Mortem Chin Strap comprising:
    a chin strap juxtaposable to a lower jaw of a deceased;
    a right ear loop secured and closed to an end of the chin strap, wherein the right ear loop is for removably engaging the deceased's right ear;
    a left ear loop secured and closed to the end of the chin strap opposite of the right ear loop, where the left ear loop is for removably engaging the deceased's left ear thereby resiliently biasing the chin strap against the lower jaw in a closed position;
    at least one right band slidably surrounding the right ear loop mesial the right ear and the chin strap, thereby allowing adjustment of the length and tension; and
    at least one left band slidably surrounding the left ear loop mesial the left ear and the chin strap, thereby allowing adjustment of the length and tension.

2. The Adjustable Post Mortem Chin Strap of claim 1, wherein the central portion of the chin strap is formed into an arcuate shape formed to the shape of the lower jaw, and where the extended ends of the chin strap taper into narrow swaged sections.

3. The Adjustable Post Mortem Chin Strap of claim 1, wherein the chin strap comprises a transparent resilient plastic.

4. The Adjustable Post Mortem Chin Strap of claim 3, wherein the chin strap comprises a tinted resilient plastic.

5. The Adjustable Post Mortem Chin Strap of claim 4, wherein the right ear loop and the left ear loop comprise an elastic material.

6. An Adjustable Post Mortem Chin Strap comprising:

a chin strap juxtaposable to a lower jaw of a deceased;

a right ear loop secured and closed to an end of the chin strap, wherein the right ear loop is for removably engaging the deceased's right ear;

a left ear loop secured and closed to the end of the chin strap opposite of the right ear loop, where the left ear loop is for removably engaging the deceased's left ear thereby resiliently biasing the chin strap against the lower jaw in a closed position;

at least three right bands spaced apart slidably surrounding the right ear loop mesial the right ear and the chin strap, thereby allowing adjustment of the length and tension;

at least three left bands spaced apart slidably surrounding the left ear loop mesial the left ear and the chin strap, thereby allowing adjustment of the length and tension;

the central portion of the chin strap is formed into an arcuate shape formed to the shape of the lower jaw, and where the extended ends of the chin strap taper into narrow swaged sections;

the chin strap comprises a transparent resilient plastic;

the chin strap comprises a tinted resilient plastic; and the right ear loop and the left ear loop comprise an elastic material.

* * * * *